United States Patent [19]
Mandai et al.

[11] Patent Number: 5,854,408
[45] Date of Patent: Dec. 29, 1998

[54] PROCESS FOR ACYLATING THE 1-POSITION OF SACCHARIDES

[75] Inventors: Tadakatsu Mandai, c/o Kurashiki Univ. of Sci. & Arts 2640, Tsurajima-cho, Nishinoura, Kurashiki-shi, Okayama-ken, 712; Hiroshi Okumoto, Kurashiki; Koji Hara, Yokohama; Katsuhiko Mikuni, Yokohama; Kozo Hara, Yokohama; Hiroki Hamada, Okayama, all of Japan

[73] Assignees: Ensuiko Sugar Refining Co., Ltd., Yokohama; Tadakatsu Mandai, Kurashiki, both of Japan

[21] Appl. No.: 868,147

[22] Filed: Jun. 3, 1997

[51] Int. Cl.$^6$ .............................. C07H 1/00; C07H 3/02; C07H 3/04
[52] U.S. Cl. ........................................ 536/18.6; 536/18.5
[58] Field of Search .................................... 536/18.5, 18.6

[56] References Cited

U.S. PATENT DOCUMENTS 3,634,392  1/1972  Lyness et al. .
4,130,709  12/1978  Nagarajan .

FOREIGN PATENT DOCUMENTS

WO95/14028  5/1995  WIPO .

OTHER PUBLICATIONS

W.H. Binder, et al., Monatshefte Fuer Chemie, Vol. 126, No. 8/9, pp. 923–932, "Synthesis of a Symmetric Multivalent Molecule containing four Carbohydrate Substituents", 1995.

Goeran Peterson, et al., Svensk Papperstidning, Vol. 72, No. 7, pp. 222–225, "Formation of Glucopyranosylglycolic Acids during the Hydrolysis of Cellulose", 1969.

N. Palma, et al., Eur. Cong. Biotechnol., Vol. 1, pp. 533–542, "Pleuromutilin Related Metabolites Produced by Submerged Culture of the Basidiomycetous Genus Cliptopilus Kummer", 1984.

*Primary Examiner*—Gary L. Kunz
*Attorney, Agent, or Firm*—Oblon, Spivak, McClelland, Maier and Neustadt, P.C.

[57] ABSTRACT

A sugar derivative wherein a hydroxy-carboxylic acid is combined to a position 1 of a sugar via ether linkage, and other hydroxyl groups are protected with a protective groups. A method of producing the sugar derivative, comprises allowing glycolic ester to react with a compound so as to combine said glycolic ester at the position 1 of the sugar skeleton, and then saponifying, said compound has on the position 1 any of hydroxyl group, halogen atom and sulfur atom with a substitutent group, and has other hydroxyl groups being protected with a protective groups.

12 Claims, No Drawings

PROCESS FOR ACYLATING THE 1-POSITION OF SACCHARIDES

FIELD OF THE INVENTION

The present invention relates to an acylating agent and a method of manufacturing thereof, and in more detail, it relates to an acylating agent comprising a sugar derivative and to a method of manufacturing said sugar derivative.

BACKGROUND OF THE INVENTION

For the purpose of improving the stability of physiologically active substances and water solubility of fat-soluble substances, extensive studies have been made for the technology of making glycosides via ether linkage, and it is a general knowledge to convert physiologically active substances to glycosides by making ether linkage by organic synthesis or enzymatic reaction (see published methods of glycosidation; for example, Chapter 3 in Series of Experimental Chemistry, 4th Edition, Volume 26 (Organic Synthesis VIII), edited by The Chemical Society of Japan). However, since the hydroxyl group in sugars has relatively low reactivity, it is a problem that the yield of the desired products is low in organic synthesis. On the other hand, in enzymatic reactions the obtainable products are limited by the substrate specificity of enzymes and in addition it is a problem that plural reaction products may be formed.

In previous methods of manufacturing glycosides, matching of aglycone and sugar was an important factor, and particularly when the aglycone is a compound containing hydroxyl, amino or other radicals it was difficult to synthesize a glycoside.

Also many cases have been reported, where synthesized glycosides do not satisfactorily contribute to the improvement of physical properties of substances, and so establishment of a more effective technique of glycosylation has been desired.

Meanwhile, acylating agent, that has been used for introducing an acyl group to an organic compound, has been generally halogenated acyl or carboxylic acid anhydride, but other active acylating agents such as other carboxylic acid derivatives and imidazolides have been the target of development.

No acylating agent containing sugar has been yet reported to date and it has not been utilized in the synthesis of glycosides.

SUMMARY OF THE INVENTION

In view of the above situation, the present inventors have made extensive studies for the novel technique of synthesizing a glycoside by using an acylating agent, and developed a novel acylating agent that allows a sugar readily to combine with a compound containing hydroxyl, amino or other radicals.

As a result, the present inventors have found that the compound, obtained by combining acetic acid to a sugar at the position 1 via ether linkage and by protecting other hydroxyl groups with a protective group, can combine with a compound containing hydroxyl, amino or other radicals, and that the product contributes to the improvement of physical properties of the original compound as desired, and they have completed the present invention.

The present invention relates to a sugar derivative wherein a hydroxycarboxylic acid is combined to a position 1 of a sugar via ether linkage, and other hydroxyl groups is protected with a protective groups.

Further the present invention provides an acetyloxyglycoside represented by the formula.1

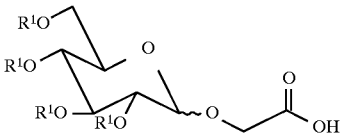

(wherein, $R^1$ is a protective group of hydroxyl groups)

Another aspect of the present invention is a method of producing a sugar derivative of claim 1, which comprises allowing glycolic ester to react with a compound so as to combine said glycolic ester at a position 1 of the sugar skeleton, and then saponifying, said compound has on the position 1 any of hydroxyl group, halogen atom and sulfur atom with a substituent group, and has other hydroxyl groups being protected with a protective group.

The present invention relates to an acylating agent comprises containing sugar derivative of claim 1.

DETAILED DESCRIPTION OF THE PREFERRED EMBODIMENTS

A sugar derivative that constitutes the acylating agent of the present invention is, as described above, the compound wherein a hydroxycarboxylic acid is combined to a position 1 of a sugar via ether linkage, and other hydroxyl groups are protected with protective groups, and it is manufactured mainly from a monosaccharide or its glycoside as the starting material. As such a sugar may be used, for example, glucose, mannose, allose, altrose, gulose, idose, galactose, talose, ribose, arabinose, xylose, lyxose, psicose, fructose, sorbose, tagatose and fucose. Maltose and other disaccharides may also be employed.

The acetyloxy glycoside that is represented by the above formula may be produced by the following reactions:

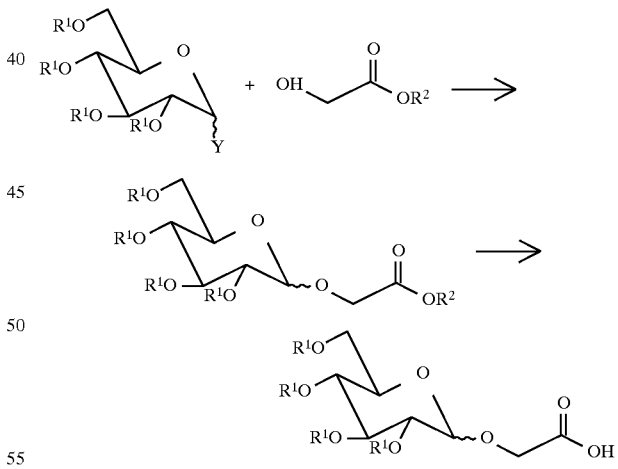

(wherein, $R^1$ is hydrogen or a protective group of hydroxyl group ordinarily employed, which is described, for example, in New Series of Experimental Chemistry, Vol. 14 (Organic Synthesis V), Chapter 11-1, edited by The Chemical Society of Japan. Y is $OR^1$ or halogen atom or sulfur atom with a substituent group. $R^2$ is a protective group of carboxylic acid, and examples thereof are methyl, ethyl, isopropyl, butyl, isobutyl, tert-butyl, monochloroethyl, monobromoethyl, trichloroethyl, benzyl, p-methylbenzyl, p-methoxybenzyl, p-nitrobenzyl, diphenylmethyl and allyl groups in addition to those that groups described in p.

152–192, Chapter 5, of "Protective Groups in Organic Synthesis" by Theodora W. Green.)

Below is explained in detail a typical embodiment of the present invention by using glucose as a sugar.

The sugar derivatives of the present invention may be produced by the following reaction steps:

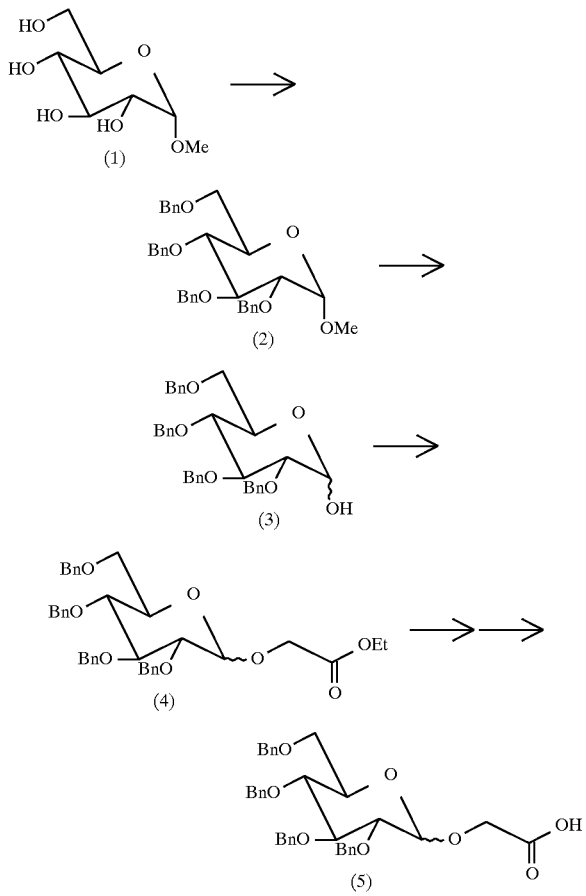

2,3,4,6-Tetrabenzyl-glucose (Compound (3), molecular weight 540.65) which is obtained, according to the conventional methods, by starting with glucose via methyl-α-glucoside (Compound (1)) and Compound (2) whose hydroxyl groups except that on the position 1 are benzylated, is allowed to react with ethyl glycolate together with p-toluenesulfonic acid in benzene at 0°–150° C., preferably at 110° C., for 0.5–50 hours, preferably for 8 hours, so as to combine ethyl glycolate to the position 1 of glucose, and an ethyl ester (Compound (4), molecular weight 626.76) is obtained.

Then, after the said compound (4) is treated with an alkali (for example, 6N NaOH) in methanol-dioxane solution at from room temperature to 100° C. for 0.5–50 hours, preferably for 3 hours, it is saponified by making acidic with hydrochloric acid (for example, 1N HCl) to obtain a corresponding carboxylic acid compound (Compound (5)). This is tetrabenzyl acetyloxy-glucoside, a sugar derivative of the present invention, which is obtained when glucose is employed as the starting material. When another sugar is employed in place of glucose, corresponding sugar derivative with different sugar skeleton may be obtained by similar reaction steps.

The sugar derivative is useful as an acylating agent and it causes acylating reaction readily with a compound having hydroxyl or amino group, for example, and gives a combined product. Hydrolysis of the product with a paradium catalyst removes the protective benzyl groups on the sugar moiety to yield desired free glycoside.

By the method described below, tetraacetyl acetyloxy-glucoside, another sugar derivative of the present invention may be manufactured.

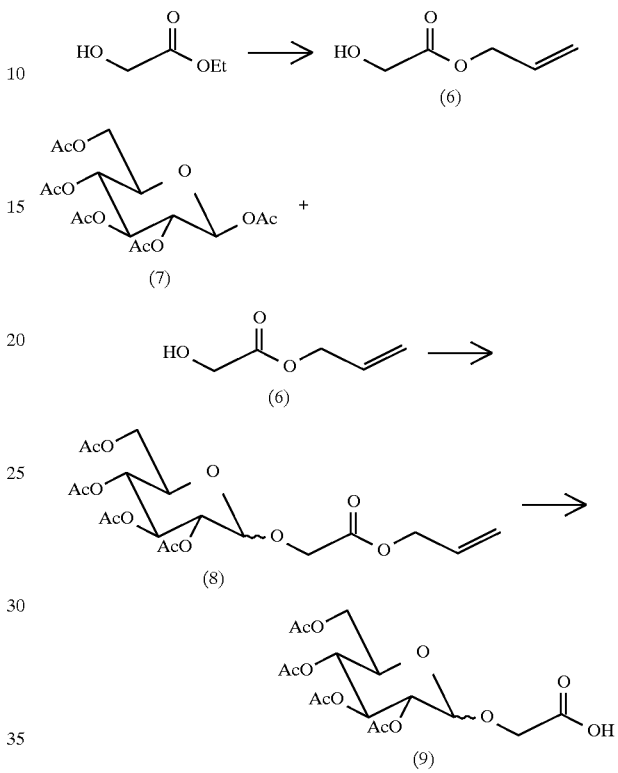

Ethyl glycolate is allowed to react with 1-chloro-3-hydroxy-tetrabutyldistanoxane and allyl alcohol at 0°–150° C., preferably at 120° C., for 0.5–50 hours, preferably for 11 hours, to obtain Compound (6). To a mixture of this compound (6) and pentaacetyl-glucose (Compound (7)), boron trifluoride-diethyl ether complex is added, and the mixture is allowed to react at 0°–100° C., preferably at 30° C., for 0.5–50 hours, preferably for 20 hours, to obtain Compound (8). To this compound (8), paradium acetate, triphenylphosphine, triethylamine and formic acid are added, and the mixture is allowed to react at 0°–100° C., preferably at 30° C., for 0.5–50 hours, preferably for 20 hours, to obtain Compound (9). This compound is tetraacetyl acetyloxy-glucoside, another sugar derivative of the present invention when glucose is used as the starting sugar. In this case also, by similar reactions with a sugar other than glucose corresponding sugar derivative with different sugar moiety may be obtained.

The sugar derivative is useful as an acylating agent, and it combines readily with a compound having hydroxyl or amino group by causing acylating reaction. Hydrolysis of the product in alkaline solution removes the modifying acetyl groups in the sugar moiety and the desired free glycoside is obtained.

A variety of compounds may be used for the conversion to glycosides by the reaction with the acylating agent of the present invention. Particularly, such physiologically active substances as paclitaxel and vitamin D, and such fat-soluble compounds as perfumes may be mentioned. The conversion of these compounds to glycosides contributes to the improvement of their stability and water solubility. For the improvement of water solubility of fat-soluble compounds, the adequate length of acyl group is that of acetyl group as described in the above acylating agent, and longer acyl chains cannot contribute to the improvement of water solubility of the compounds. However, for the use to improve other physical properties, employment of another substance, in place of glycolic ester that serves as a spacer, will produce another acylating agent with a different acyl chain length, and it is recommended to select an acylating agent suitable for the specific purpose.

In this way, the use of the acylating agent of the present invention produces readily glycosides in which a sugar is combined via a spacer, and it greatly contributes to the improvement of such physical properties as water solubility and stability by the glycosylation.

By the present invention, a sugar derivative is provided, which combines a hydroxycarboxylic acid on the position 1 of the sugar via ether linkage and whose other hydroxyl groups are protected. This compound may be used as an acylating agent for allowing to react with various substances to convert them into glycosides, and by this process, it can be used for the improvement of physical properties of the said substances.

EXAMPLE

The present invention will be described in more detail by means of the following examples, which however are not intended to restrict the scope of the invention Example 1

2,3,4,6-Tetrabenzyl-glucose (Compound (3), $C_{34}H_{36}O_6$, molecular weight 540.65) (1.62 g) which was obtained by the conventional method, ethyl glycolate (1.56 g), p-toluenesulfonic acid (0.10 g) and benzene (80 ml) were allowed to react at 110° C. under refluxing for 8 hours to obtain the ethyl ester (Compound (4), $C_{38}H_{42}O_8$, molecular weight 626.74).

Then, this compound (1.88 g) was allowed to react with 6N NaOH (10 ml) in methanol (10 ml) and dioxane (15 ml) at room temperature—100° C. for 3 hours, and its deethylation by bringing it into 1N HCl (80 ml) produced the carboxylic acid compound (Compound (5), $C_{36}H_{38}O_8$, molecular weight 598.69).

Compound (5) was dissolved in deuterium chloroform for subjecting to analysis by $^1$H-NMR and each peak was assigned for the determination of structure, confirming that it is represented correctly by the above-described structure. Data are given below.

$^1$H-NMR (500 MHz, CDCl$_3$) of the carboxylic compound:
3.35–3.80 (m, 5H), 3.90–4.95 (m, 10H), 7.00–7.40 (m, 20H, Ar)

Example 2

To ethyl glycolate (10 mmol), 1-chloro-3-hydroxytetrabutyldistanox ane (30 mg) and allyl alcohol (5 ml) were added and stirring of the mixture at 120° C. for 11 hours gave Compound (6). Then this compound (3 mmol) and pentaacetyl-glucose (2 mmol) were dissolved in methylene chloride (8 ml), and after dropping boron trifluoride-diethyl ether complex (2.4 mmol) the mixture was stirred at room temperature for 20 hours to obtain Compound (8). This compound (1.1 mmol) was dissolved in tetrahydrofuran (THF) (5 ml) and then paradium acetate (0.1 mmol), triphenylphosphine (0.3 mmol), triethylamine (5 mmol) and formic acid (4 mmol) were added successively, and the mixture was stirred at room temperature for 20 hours to obtain Compound (9), namely the carboxylic acid compound (tetraacetyl acetyloxy-glucoside).

This carboxylic acid compound was dissolved in deuterium chloroform and subjected to analysis by $^1$H-NMR. By assigning each peak the structure was determined and it was confirmed to be represented correctly by the above shown structure. Data are shown below.

$^1$H-NMR (500 MHz, CDCl$_3$) of the carboxylic compound:
2.02–2.10 (m, 12H), 3.69–3.77 (m, 1H), 4.10–4.18 (m, 1H), 4.22–4.40 (m, 3H), 4.67 (d, J=7.6, 1H), 5.01–5.15 (m, 2H), 5.23–5 28 (m, 1H)

Example 3

By using benzyl acetyloxy-glucoside which is represented by Compound (5) and obtained in Example 1 as an acylating agent. 1-menthol was converted into glucoside. Reaction steps are as shown below.

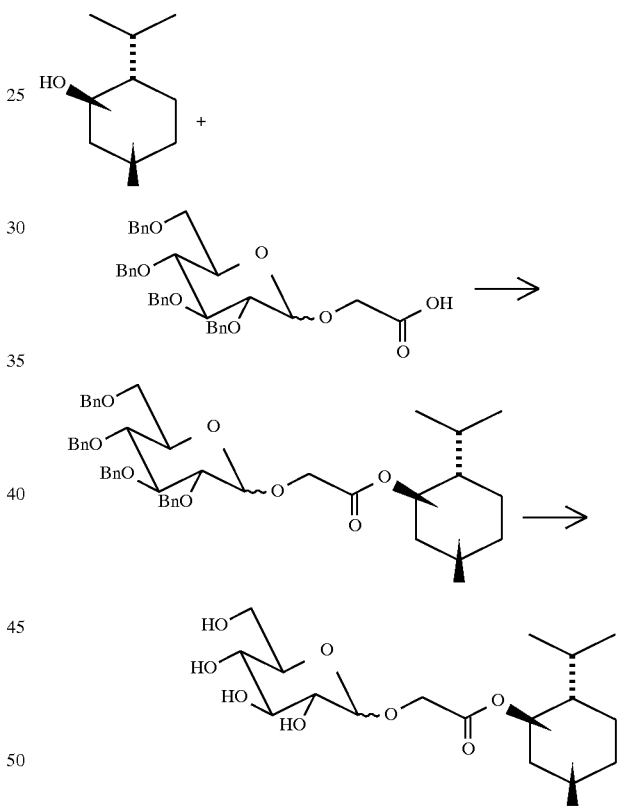

1-Menthol (1 mmol) was dissolved in methylene chloride (5 ml) and dicyclohexylcarbodiimide (DCC) (2 ml) and 4-N,N-dimethylaminopyridine (DMAP) (2 mmol) were added. Then benzyl acetyloxy-glucoside (2 mmol) was added and the mixture was stirred at room temperature for 8 hours. The reaction mixture was poured into saturated aqueous sodium chloride solution, extracted with ethyl acetate and treated by the conventional method to obtain 1-menthol-glucoside.

Then the reaction Product was debenzylated by using paradium/carbon in ethanol to obtain free glucoside.

1-Menthol-glucoside thus obtained was found to have about 200 times higher water solubility than 1-menthol itself.

Example 4

By using tetraacetyl acetyloxy-glucoside obtained in Example 2 as an acylating agent glucosylation of 1-menthol was performed. The reaction steps are as follows:

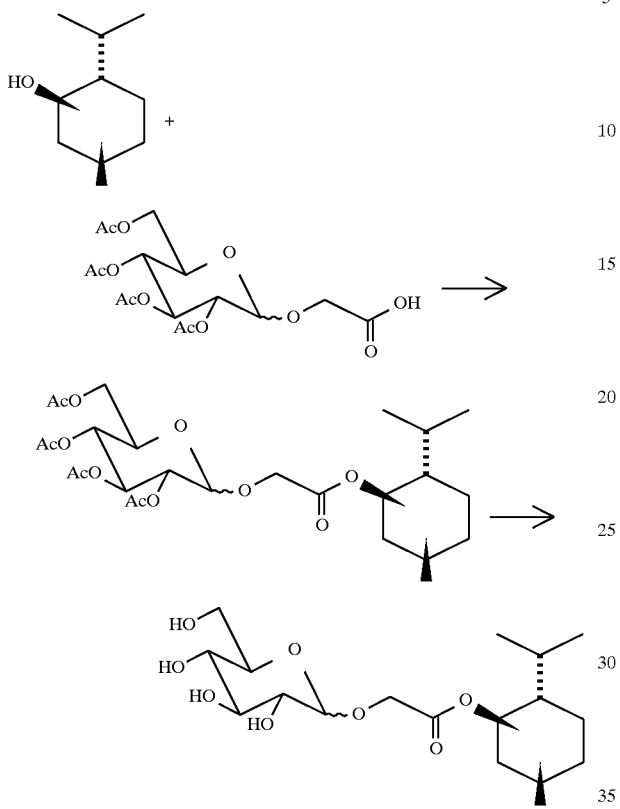

1-Menthol (1 mmol) was dissolved in methylene chloride (5 ml) and DCC (2 ml) and DMAP (2 mmol) were added. Then tetraacetyl acetyloxy-glucoside (2 mmol) was added and the mixture was stirred at room temperature for 8 hours. The reaction mixture was poured into saturated aqueous solution of sodium chloride, and after extracting with ethyl acetate, 1-menthol-glucoside was obtained by the treatment of the conventional method.

The reaction product was deacetylated in ethanol with 0.1 N sodium hydroxide to obtain free glucoside.

1-Menthol glcoside thus obtained was found to have about 200 times higher solubility in water than 1-menthol itself.

What is claimed is:

1. A method of producing a sugar derivative having a hydroxy-carboxylic acid residue bonded to the 1-position of the sugar via the hydroxyl group thereof, comprising:

(a) reacting a hydroxy-carboxylic acid ester with a sugar having a hydroxyl group or a halogen atom at the 1-position thereof, to form an ether linkage between the hydroxyl group of the hydroxy-carboxylic acid ester and the carbon atom at the 1-position of the sugar, wherein, when the sugar has other hydroxyl groups, said other hydroxyl groups are protected as benzyl ethers; and (b) saponifying said ester.

2. The method of claim 1, wherein the sugar is selected from the group consisting of glucose, mannose, allose, altrose, gulose, idose, galactose, talose, ribose, arabinose, xylose, lyxose, psicose, fructose, sorbose, tagatose, fucose and maltose.

3. The method of claim 1, wherein the hydroxy-carboxylic acid ester is a glycolic acid ester.

4. The method of claim 1, wherein the hydroxy-carboxylic acid ester is the ethyl or allyl ester of glycolic acid.

5. The method of claim 1, wherein the sugar has a hydroxyl group at the 1-position thereof.

6. The method of claim 1, wherein the sugar has a halogen atom at the 1-position thereof.

7. The method of claim 1, wherein the hydroxy-carboxylic acid ester is the methyl, ethyl, isopropyl, butyl, isobutyl, tert-butyl, monochloroethyl, monobromoethyl, trichloroethyl, benzyl, p-methylbenzyl, p-methoxybenzyl, p-nitrobenzyl, diphenylmethyl or allyl ester of glycolic acid.

8. The method of claim 1, wherein the sugar derivative is represented by the formula

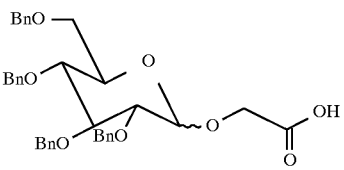

wherein Bn is a benzyl group.

9. The method of claim 1, wherein step (a) is conducted at 0° to 150° C.

10. The method of claim 9, wherein step (a) is conducted for 0.5 to 50 hours.

11. The process of claim 1, wherein step (b) is accomplished with an alkali in a methanol-dioxane solution.

12. The process of claim 11, wherein step (b) is conducted at a temperature from room temperature to 100° C. for 0.5 to 50 hours.

* * * * *